United States Patent [19]
Weigert

[11] 4,313,003
[45] Jan. 26, 1982

[54] PREPARATION OF DIMETHYLAMINE

[75] Inventor: Frank J. Weigert, Wilmington, Del.

[73] Assignee: E. I. Du Pont de Nemours and Company, Wilmington, Del.

[21] Appl. No.: 154,482

[22] Filed: Jun. 6, 1980

Related U.S. Application Data

[63] Continuation-in-part of Ser. No. 74,419, Sep. 11, 1979, abandoned.

[51] Int. Cl.$^3$ .............................................. C07C 91/02
[52] U.S. Cl. .................................................... 564/463
[58] Field of Search ......................................... 564/463

[56] References Cited
U.S. PATENT DOCUMENTS 1,926,691  9/1933  Swallen et al. ..................... 564/469

OTHER PUBLICATIONS

Restelli et al., "A. I. Ch. E. Journal", 12, No. 2, 3/1966, pp. 292-296.

*Primary Examiner*—Paul F. Shaver

[57] ABSTRACT

Improved continuous process for disproportionating monomethylamine to dimethylamine and ammonia, said process comprising passing monomethylamine over the crystalline aluminosilicate catalyst selected from
  (a) mordenite wherein the primary cation is Na, HNa having at least 2% Na, Mg, Ca, Sr or Ba
  (b) ferrierite wherein the primary metal cation is Na, K, Mg, Ca, Sr or Ba
  (c) clinoptilolite and
  (d) phillipsite,
at a temperature of 250°-475° C. and a pressure of 7-7000 kPa, at a feed rate of 0.1-10 g of monomethylamine/g of catalyst per hour, at a monomethylamine conversion of 15-75%.

9 Claims, 3 Drawing Figures

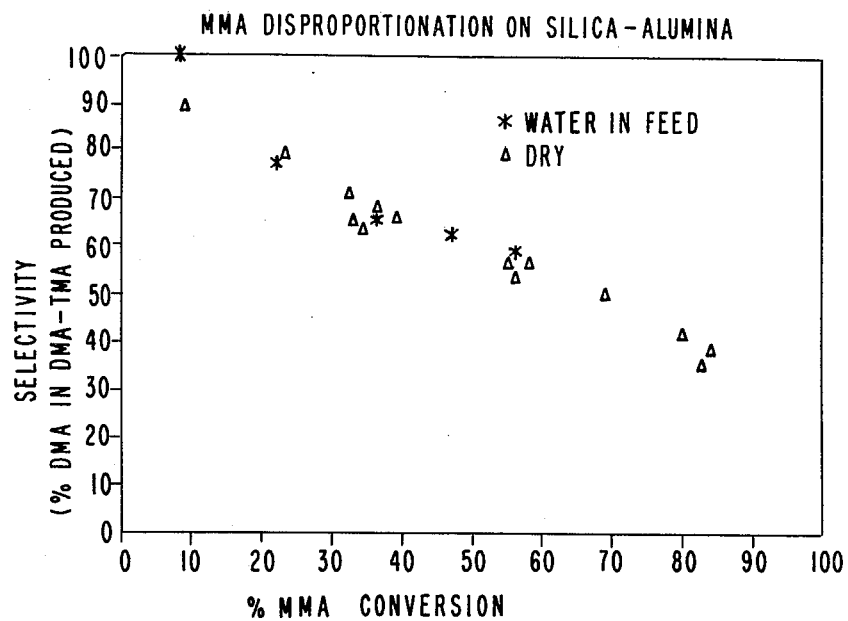
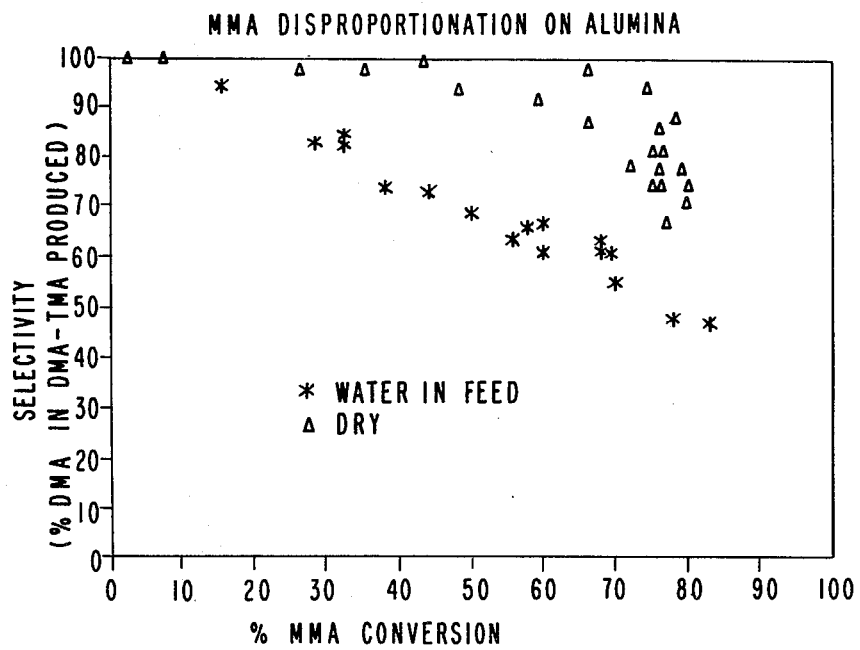

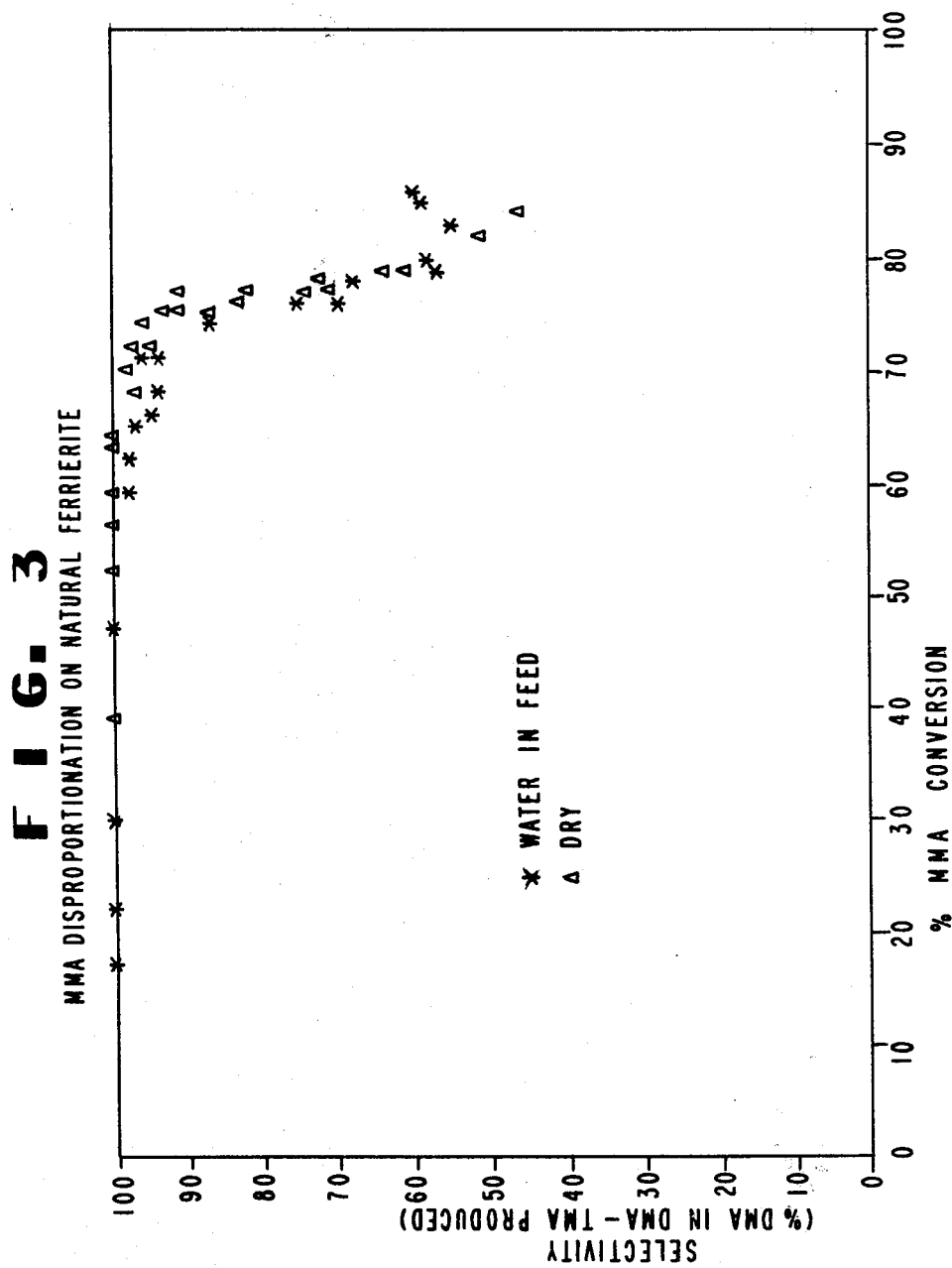

PREPARATION OF DIMETHYLAMINE

CROSS-REFERENCE TO RELATED APPLICATION

This application is a continuation-in-part of application Ser. No. 74,419 filed Sept. 11, 1979 and now abandoned.

DESCRIPTION

1. Technical Field

This invention relates to an improved preparation of dimethylamine by a catalytic disproportionation of monomethylamine.

2. Background

It is well known in the art that the catalyzed reaction of methanol and ammonia can be employed to produce mono-, di- and/or trimethylamine. To facilitate the formation of any one of the methylamines various expedients can be used. For example, it is known that the use of dimethyl ether in conjunction with or in place of methanol, recycling unwanted methylamines, the use of varying molar ratios of the reactants and the use of specific dehydrating or aminating catalysts can be employed to alter the relative amounts of the various amines in the product.

Exemplary, but not intended to be all inclusive, of such art, U.S. Pat. No. 3,278,598 discloses an improved, Raney nickel-catalyzed, liquid phase process of reacting primary and secondary alcohols and ammonia, the improvement comprising the use of a rhodium, palladium or ruthenium cocatalyst, to provide increased formation of secondary amine. Similarly, U.S. Pat. No. 3,387,032 discloses a catalytic process for providing increased amounts of dimethylamine from methanol and/or dimethyl ether and ammonia, using as the catalyst a silica gel-based alumina which has been partially steam deactivated and then impregnated with silver phosphate, rhenium heptasulfide, molybdenum sulfide or cobalt sulfide. U.S. Pat. Nos. 2,394,515 and 2,394,516 disclose catalytic processes for preparing polyalkylamines, with lesser quantities of the monoalkylamine, from an alcohol and/or ether of 1-5 carbon atoms and ammonia, using as the catalyst an aluminum oxide or salt which has been coated, first with silica and then with a vanadium salt or molybdenum oxide. The related U.S. Pat. No. 2,349,222 utilizes as the catalyst a granular alumina which has been coated with a nickel, cobalt or chromium oxide hydrogenation/dehydrogenation catalyst. U.S. Pat. No. 2,456,599 discloses that higher amounts of mono- and dimethylamine, and a reduced amount of trimethylamine, can be achieved in the catalyzed process wherein water is introduced along with the methanol and ammonia. U.S. Pat. No. 1,799,722 and U.S. Pat. No. 19,632 disclose catalytic processes wherein trimethylamine is introduced with the methanol and ammonia to suppress the formation of trimethylamine and provide increased amounts of dimethylamine. U.S. Pat. No. 1,992,935 discloses a catalytic process for preparing a mixture of primary, secondary and tertiary methylamines, principally dimethylamine, from methanol and ammonia, using as the catalyst a dehydrating oxide supported on a porous rigid gel such as silica gel. British 422,563 discloses a catalytic process for producing secondary amine by employing the primary amine as starting material in addition to ammonia and alcohol.

Restelli et al. in A.I.Ch.E. Journal, Vol. 12, No. 2, 292-296, March, 1966, describe studies of transmethylation reactions of monomethylamine and dimethylamine over montmorillonite, a hydrated magnesium/calcium oxide-containing aluminosilicate. With the reactions being carried out at about 320-371° C., at low conversions the monomethylamine is converted to dimethylamine, the rate being directly proportional to the amine partial pressure, thus indicating that adsorption of monomethylamine on the catalyst surface is rate-determining.

U.S. Pat. No. 1,926,691 discloses the disproportionation of monomethylamine over oxide catalysts, including aluminum silicate (silica-alumina) and partially dehydrated alumina. In the only example given, the disproportionation of monomethylamine over anhydrous alumina is highly selective for the production of dimethylamine. All the oxide catalysts disclosed are suggested to be equivalent in this regard, being broadly classified as amination catalysts.

U.S. Pat. No. 3,384,667 discloses a process for producing monosubstituted and disubstituted amines, in preference to trisubstituted amines, by reacting an alcohol and ammonia over a dehydrated crystalline aluminosilicate catalyst having pores of a diameter that pass the monosubstituted and disubstituted amine produces but not the trisubstituted amine products. The related U.S. Pat. No. 4,082,805 discloses a process for producing primary aliphatic amines, in preference to secondary and tertiary amines, from a $C_1$–$C_5$ alcohol or ether and ammonia over a natural or synthetic dehydrated crystalline aluminosilicate having the structure of ZSM-5, ZSM-11 or ZSM-21, at 300°–500° C. at one atmosphere to 1000 psig pressure, the feeds of alcohol or ether and ammonia being within the ratio 1:1 to 5:1.

Methylamines presently are generally produced commercially by a continuous process from methanol and ammonia, using an amorphous silica-alumina catalyst. At moderate methanol conversions such processes generally produce more trimethylamine than mono- and dimethylamine (at very low conversions monomethylamine is the major product). Because of its greater usage industrially as a chemical intermediate dimethylamine is the most desirable methylamine product, with monomethylamine being next most preferred. Production of the maximum amounts of monomethylamine and dimethylamine is achieved when equilibrium is reached, at about 100% methanol conversion. However, the relative amounts of the three amines produced at equilibrium depend, to a large extent, on the carbon/nitrogen (C/N) ratio, that is, the methanol/ammonia ratio in the reactants. At carbon/nitrogen ratios of about one the product mixture contains, on a mole basis, about 55% ammonia, 22% trimethylamine (TMA), 12% monomethylamine (MMA) and 12% dimethylamine (DMA). The product mixture can be separated and the less desirable methylamines can be recycled. However, recycling monomethylamine provides only about 10% dimethylamine per pass, at renewed equilibrium, with most of the monomethylamine being converted to trimethylamine and ammonia. At no C/N ratio, at equilibrium, is dimethylamine the favored product.

The synthesis of methylamines is distinguishable from the synthesis of ethylamines. For example, the thermodynamics of the ethylamine reactions corresponding to those discussed above are such that the formation of diethylamine is favored at an ethyl/nitrogen ratio of about 2. Thus, the production of dimethylamine is substantially more complex and difficult than is the production of diethylamine, using similar processes.

An object of this invention, therefore, is to provide an improved process for converting monomethylamine directly to dimethylamine and ammonia, to the substantial exclusion of trimethylamine, thus obviating production of the least desirable methylamine and the concomitant recovery and recycling processes associated therewith. Another object is to provide a process which uses a catalyst which can accomplish this objective in the presence of water, such as water which may be present along with the monomethylamine. Other objects will become apparent hereinafter.

BRIEF DESCRIPTION OF DRAWINGS

The accompanying drawings forming a material part of this disclosure provide plots showing the selectivity of the catalyst of the invention process (FIG. 3), as compared to the use of a conventional amorphous silica-alumina catalyst (FIG. 1) and a conventional alumina catalyst (FIG. 2), both of which are outside the invention, in converting monomethylamine to dimethylamine.

More specifically, the drawings provide plots showing the percentages of dimethylamine in the dimethylamine/trimethylamine products obtained at varying conversions of monomethylamine. The drawings are based on data provided in the examples and experiments. The silica-alumina catalyst represented in FIG. 1 may be seen to be non-selective whether the system is dry or contains water. The alumina catalyst represented in FIG. 2 may be seen to be selective when dry but non-selective when water is present in the system. The natural ferrierite catalyst represented in FIG. 3 may be seen to be selective whether the system is dry or contains water.

DISCLOSURE OF INVENTION

For further comprehension of the invention, and of the objects and advantages thereof, reference may be made to the following description and accompanying drawings and to the appended claims in which the various novel features of the invention are more particularly set forth.

The invention herein resides in an improved catalytic process, for example, over that of U.S. Pat. No. 1,926,691, for preparing dimethylamine from monomethylamine. More specifically, it has been discovered that the general class of catalysts commonly referred to as amination catalysts can be divided into three categories according to their selectivities in the monomethylamine disproportionation reaction and their sensitivities to water.

| Class | Selectivity | |
|---|---|---|
| | Dry | Wet ($H_2O$) |
| III | Good | Good |
| II | Good | Poor |
| I | Poor | Poor |

Class I catalysts, exemplified by silica-alumina, hydrogen-exchanged zeolites, and some neutral zeolites, such as the Zeolite A's, offretite and faujasite, are non-selective. Catalysts of Class II, such as alumina and the zeolite erionite, are selective with anhydrous feeds, but they lose their selectivities in the presence of water. Several zeolites belonging to Class III retain their high selectivities even when water is present in the system.

Still more specifically, the invention resides in an improved continuous process wherein monomethylamine is disproportionated to dimethylamine and ammonia over the crystalline aluminosilicate (Zeolite) catalyst selected from (a) mordenite wherein the primary cation is Na, HNa having at least 2% Na by weight (for example, 2-4.3% Na), Mg, Ca, Sr or Ba (b) ferrierite wherein the primary metal cation is Na, K, Mg, Ca, Sr or Ba (c) clinoptilolite and (d) phillipsite, at a temperature of 250°-475° C. and a pressure of 1-1000 psi (7-7000 kPa), at a feed rate of 0.1-10 g of monomethylamine/gram of catalyst per hour. Preferably, the process is carried out with substantially anhydrous monomethylamine and a ferrierite catalyst at 350°-400° C. and 10-500 psi (70-3000 kPa), especially 300 psi (2000 kPa), at a feed rate of 0.5-2 g, especially 1 g, of monomethylamine/gram of catalyst per hour.

Most of the catalysts which are useful herein are commonly available or can be prepared readily by one skilled in the art. Following are examples of preparative procedures which can be employed.

Sodium-hydrogen mordenite can be prepared by admixing sodium mordenite extrusions and aqueous hydrochloric acid, in appropriate amounts, allowing the mixture to stand overnight, removing the solids by filtration, washing the recovered solids with distilled water, and then air drying and calcining the solids at 400° C. for four hours.

Calcium mordenite can be prepared by refluxing an aqueous calcium chloride solution (25 grams of calcium chloride in 150 ml of distilled water) containing 20 grams of sodium mordenite for three days, decanting the supernatant, adding fresh aqueous calcium chloride solution, refluxing another three days, removing the solids by filtration, washing the recovered solids with distilled water to remove chloride, and then air drying and calcining the solids.

Other crystalline aluminosilicates (Zeolites), such as magnesium, strontium or barium mordenite and magnesium, calcium, strontium or barium ferrierite can be prepared by an exchange reaction by refluxing 10 grams of the appropriate Zeolite and 10 grams of the appropriate nitrate salt in 100 ml of water, removing the solids by filtration, washing the recovered solids with distilled water, and then drying the solids for two hours at 110° C., two hours at 200° C. and 4 hours at 400° C.

Process variables of this invention include temperature, pressure and contact time. If the temperature is too low, the conversion of monomethylamine to dimethylamine will be low. If the temperature is too high, equilibration and coking (carbonization) may result unless the contact time is reduced. Unduly large reaction vessels are required if the process is carried out at very low pressures, and the products must be refrigerated to condense them for further purification; costly thick-walled vessels are required at excessively high pressures. Short contact times result in low monomethylamine conversions and long contact times may result either in inefficient use of catalyst at low temperatures, or equilibration and coking at high temperatures. Generally, contact times of 0.1-60 seconds, normalized to 7 kPa pressure, are satisfactory, with 1-10 seconds being preferred.

The efficiency of the catalyst employed herein is defined by the conversion of monomethylamine and the selectivity to dimethylamine. As the terms are used herein, conversion, in %, is 100−100×[MMA/(NH$_3$+MMA+DMA+TMA)] and selectivity, in %, is 100×[DMA/(DMA+TMA)]. Stated in another way, conversion is determined from the amount of monomethylamine (considered to be unconverted) in the product mixture of ammonia and the three amines. Selectivity is determined from the amount of dimethylamine relative to the dimethylamine and trimethylamine in the product mixture, that is, the amount of secondary amine which is produced from that portion of the monomethylamine which has been converted.

Conversion of monomethylamine in the process of the invention is dependent on flow rate (contact time), temperature and pressure. Optimum results are achieved by selecting conditions which represent a compromise of these variables. In the accompanying FIGS. 1, 2 and 3 which represent a part of this disclosure are depicted plots of selectivity vs. conversion, as defined above, for a variety of experiments carried out at atmospheric pressure at a variety of temperatures and flow rates using as the catalyst a conventional amorphous silica-alumina (FIG. 1) and alumina (FIG. 2), both representative of the art, and a crystalline natural ferrierite, representative of a catalyst of the process of the invention. At uneconomically low levels of monomethylamine conversion, for example, below about 10%, the selectivity is high for all three of the aforesaid classes of catalysts, whether the system is anhydrous or contains water; that is, the processes favor the formation of dimethylamine. Correspondingly, at high levels of monomethylamine conversion, for example, above about 75%, the selectivity is low for all three classes of catalysts, whether the system is anhydrous or contains water, because amines equilibration is approached and possibly coking occurs. At commonly used conversion levels, for example, 15-75%, the process of the invention provides selectivities which are substantially superior to those which are obtained with known catalysts, particularly in the presence of water, a feature not exhibited by processes employing alumina as the catalyst, for example, as disclosed in U.S. Pat. No. 1,926,691, or natural erionite as the catalyst, for example, as demonstrated hereinafter in Experiment 4. The usefulness of the catalyst of the process of the invention in the presence of water is particularly significant in that recycled monomethylamine streams which are isolated from the reaction of methanol and ammonia and which can be used herein as the feed stream may contain water.

The following examples are provided to illustrate specific embodiments of the invention. Some of the examples include experiments which demonstrate processes outside the invention, for comparison.

EXAMPLE 1

Monomethylamine (MMA) was passed over 3 g of sodium mordenite, at atmospheric pressure, a temperature of 300°-450° C. and a flow rate of 0.11 to 0.83 g of MMA/g of catalyst/hour, in a Vycor ® tubular reactor having a 0.5 inch (1.3 cm) diameter and a 3 inch (7.6 cm) deep zone heated with a split tube furnace. The three amines and ammonia were determined by gas chromatography using a 10 foot (3.0 m)×0.125 inch (0.32 cm) column of polyethylene oxide (25% Carbowax ® 400), 2.5% NaOH on 80/100 mesh diatomaceous earth (Chromosorb ® WAW). Elution takes place within four minutes at 65° C. with a He flow rate of 20 ml/minute in the order: TMA, NH$_3$, DMA, MMA. The data obtained are shown in Table I.

TABLE I

| Temp. °C. | Flow Rate g MMA/g catalyst/hr | MMA Conversion | Selectivity |
|---|---|---|---|
| 300 | 0.11 | 69 | 77 |
| 325 | 0.24 | 8* | 100 |
| 350 | 0.66 | 43 | 95 |
| 350 | 0.47 | 58 | 97 |
| 350 | 0.25 | 65 | 95 |
| 375 | 0.83 | 39 | 98 |
| 375 | 0.29 | 66 | 97 |
| 375 | 0.55 | 68 | 93 |
| 400 | 0.81 | 77* | 87 |
| 400 | 0.81 | 47 | 97 |
| 400 | 0.62 | 81* | 58 |
| 400 | 0.43 | 83* | 47 |
| 425 | 0.67 | 83* | 72 |
| 450 | 0.81 | 75 | 86 |
| 450 | 0.67 | 87* | 70 |

*outside the range 15-75%.

Selection of process conditions is important. As the temperature reaches the 400°-450° C. range, MMA conversion is about 80% or higher but, because TMA-rich equilibrium conditions are approached, selectivity drops. If the temperature is maintained in the lower range of operability, MMA conversion is unacceptably low, for example, less than 15% but the selectivity approaches 100%. Preferably, process conditions are selected to provide an MMA conversion of at least 15% and a selectivity of at least 80%. With Na mordenite, selectivities of greater than 80% can be obtained at 250°-450° C. and atmospheric pressure with feed rates of 1 to 10 g of MMA/g of catalyst/hour.

EXAMPLE 2

Using procedures substantially the same as those described in Example 1 MMA was passed over various catalysts falling within the scope of the present invention. Shown in Table II are data for these as well as for control runs using catalysts which are outside the invention, namely, calcium erionite, erionite, $\gamma$-Al$_2$O$_3$, $\eta$-Al$_2$O$_3$, sodium hydrogen mordenite with less than 2% Na, hydrogen mordenite, the standard amine catalyst amorphous SiO$_2$/Al$_2$O$_3$, Bentonite Volclay, Chabazite-erionite, Pd/SiO$_2$, and Zeolites 4A, 5A and Na-ZSM-5. The control runs are designated "C.".

TABLE II

| Catalyst | Flow Rate g MMA/g catalyst/hr | Temp. (°C.) | MMA Conversion | Selectivity |
|---|---|---|---|---|
| C. Calcium Erionite | 0.69 | 300 | 16 | 98 |
| | 0.69 | 350 | 45 | 94 |
| | 0.69 | 400 | 80* | 62 |
| Clinoptilolite | 0.69 | 300 | 52 | 80 |
| | 0.69 | 395 | 91* | 55 |
| Barium Mordenite (Ba = 14.1%, Na = 1.9%) | 0.35 | 294 | 31 | 100 |
| | 0.35 | 398 | 72 | 67 |
| Magnesium Mordenite | 0.69 | 287 | 24 | 100 |
| | 0.69 | 347 | 62 | 87 |
| Calcium Mordenite | 0.69 | 369 | 37 | 91 |
| | 0.69 | 404 | 66 | 76 |
| Phillipsite | 0.69 | 350 | 21 | 93 |
| | 0.69 | 400 | 27 | 93 |
| C. Erionite | 0.69 | 313 | 44 | 84 |
| | 0.69 | 356 | 81* | 58 |
| Strontium Mordenite | 0.69 | 300 | 18 | 100 |
| | 0.69 | 350 | 42 | 97 |
| Hydrogen | 0.69 | 300 | 37 | 100 |

TABLE II-continued

| Catalyst | Flow Rate g MMA/g catalyst/hr | Temp. (°C.) | MMA Conversion | Selectivity |
|---|---|---|---|---|
| Sodium Mordenite (at least 2% Na) | 0.69 | 342 | 43 | 90 |
| Ferrierite | 0.77 | 250 | 17 | 100 |
|  | 0.77 | 275 | 22 | 100 |
|  | 0.74 | 300 | 30 | 100 |
|  | 0.74 | 325 | 47 | 100 |
|  | 0.71 | 350 | 59 | 98 |
|  | 0.75 | 375 | 65 | 97 |
|  | 0.77 | 400 | 71 | 94 |
|  | 0.73 | 425 | 74 | 87 |
|  | 0.35 | 425 | 78* | 68 |
|  | 0.35 | 350 | 66 | 95 |
|  | 0.86 | 385 | 62 | 98 |
| C. γ-Al₂O₃ | 0.67 | 345 | 43 | 100 |
|  | 0.67 | 394 | 77* | 88 |
| C. η-Al₂O₃ | 0.69 | 300 | 26 | 97 |
|  | 0.69 | 350 | 77* | 67 |
| Sodium Mordenite (3.97% Na) | 0.69 | 256 | 19 | 100 |
|  | 0.69 | 300 | 47 | 92 |
|  | 0.69 | 340 | 64 | 81 |
| Hydrogen Sodium Mordenite (2.31% Na) | 0.69 | 234 | 28 | 95 |
|  | 0.69 | 250 | 58 | 85 |
|  | 0.69 | 300 | 84* | 52 |
| Natural Mordenite | 0.86 | 300 | 18 | 100 |
| C. Hydrogen Sodium Mordenite (1.06% Na) | 0.69 | 238 | 19 | 84 |
|  | 0.69 | 264 | 50 | 65 |
|  | 0.69 | 297 | 72 | 44 |
| C. Hydrogen Mordenite | 0.69 | 212 | 4* | 67 |
|  | 0.69 | 242 | 26 | 70 |
|  | 0.69 | 270 | 59 | 50 |
|  | 0.69 | 302 | 83* | 34 |
|  | 0.69 | 350 | 85* | 29 |
| C. 87% SiO₂/13% Al₂O₃ | 0.23 | 250 | 33 | 63 |
|  | 0.78 | 275 | 9 | 89 |
|  | 0.75 | 300 | 23 | 79 |
|  | 0.75 | 325 | 36 | 68 |
|  | 0.77 | 350 | 58 | 56 |
|  | 0.73 | 375 | 69 | 50 |
| C. 87% SiO₂/13% Al₂O₃ | 0.77 | 375 | 80* | 42 |
|  | 0.77 | 400 | 87* | 38 |
|  | 0.43 | 300 | 55 | 57 |
|  | 0.17 | 300 | 87* | 36 |
|  | 0.64 | 300 | 39 | 66 |
|  | 0.43 | 300 | 56 | 54 |
|  | 0.17 | 225 | 33 | 65 |
|  | 0.86 | 300 | 32 | 71 |
| C. Bentonite Volclay | 0.17 | 300 | 69 | 46 |
|  | 0.17 | 330 | 76* | 40 |
|  | 0.17 | 360 | 82* | 36 |
|  | 0.17 | 276 | 56 | 55 |
|  | 0.17 | 250 | 36 | 67 |
| C. Chabazite erionite | 0.86 | 300 | 5* | 100 |
| C. 2% Pd/98% SiO₂ | 0.86 | 300 | 1* | 100 |
| C. 4A Zeolite | 0.86 | 300 | 3* | 100 |
| C. 5A Zeolite | 0.86 | 300 | 48 | 64 |
| C. Zeolite Na-ZSM-5 | 0.86 | 300 | 59 | 52 |

*outside the range 15-75%

EXAMPLE 3

As indicated above the monomethylamine being disproportionated preferably is anhydrous. The purpose of this example is to demonstrate that the catalyst of the process of this invention is relatively insensitive to water. Thus, the monomethylamine starting material need not be anhydrous. Although, as can be seen from Table III, water in the MMA (60% H₂O, 40% MMA) has no apparent effect on the selective disproportionation of MMA over sodium mordenite, it does have an effect in the case of η-Al₂O₃ which is outside the invention. Other examples and experiments included herein further show this distinction between the catalyst of the invention and the catalysts of the art. The data shown in Table III were obtained using: 3 g of sodium mordenite or η-Al₂O₃, a liquid feed (40% MMA in H₂O) of 3 ml/hour and 10 ml/minute of nitrogen as carrier in an apparatus identical with that described in Example 1.

TABLE III

| Catalyst | Temp. (°C.) | MMA Conversion | Selectivity |
|---|---|---|---|
| Sodium Mordenite | 275 | 64 | 63 |
| Sodium Mordenite | 300 | 50 | 100 |
| Sodium Mordenite | 325 | 62 | 58 |
| Sodium Mordenite | 200 | 46 | 93 |
| Sodium Mordenite | 250 | 38 | 97 |
| Sodium Mordenite | 250 | 16 | 76 |
| Sodium Mordenite | 300 | 75 | 68 |
| Sodium Mordenite | 250 | 73 | 83 |
| η-Al₂O₃ | 380 | 32 | 85 |
| " | 390 | 38 | 75 |
| " | 400 | 50 | 69 |
| " | 411 | 60 | 61 |
| " | 420 | 70 | 55 |

EXAMPLE 4

In this example, a preferred MMA disproportionation catalyst, sodium mordenite, was used. The anhydrous MMA was fed at rates of 0.45 to 1.15 g/g of Na mordenite/hour as a heated vapor to a 150 l cylindrical reactor, 0.125 inch (0.32 cm) × 6 inch (15.2 cm), containing 120 g of sodium mordenite as 0.125 inch (0.32 cm) extrusions, at a pressure of 100–350 psig (700–2400 kPA) and a temperature of about 300° C. The reactor temperature was controlled by a thermocouple in the center of the catalyst bed. Analyses were carried out by gas chromatography as described in Example 1. The experimental results are summarized in Table IV.

TABLE IV

| Pressure (kPa) | MMA Feed Rate (g/g/hr) | Temp. (°C.) | MMA Conversion | Selectivity |
|---|---|---|---|---|
| 2400 | 0.95 | 288 | 10* | 100 |
|  |  | 292 |  |  |
|  |  | 296 |  |  |
| 2400 | 1.15 | 300 | 34 | 98 |
| 2400 | 0.60 | 300 | 66 | 90 |
| 1400 | 0.60 | 300 | 58 | 96 |
| 1400 | 0.45 | 300 | 61 | 94 |
| 700 | 0.45 | 300 | 37 | 98 |

*outside the range 15-75%

EXAMPLES 5-10

These examples demonstrate that the process of the invention can be carried out either with anhydrous MMA or in a system which contains water. It may be seen from the results that the catalyst is effective in either system. The process conditions were substantially as described in Example 1. Data for these examples are summarized in Tables V–X, respectively. It is to be understood that some of the data in these tables may be repetitious of data provided in Tables I-IV.

TABLE V

SODIUM MORDENITE CATALYST WITHOUT WATER IN THE FEED

| Flow Rate g MMA/g cat/h | Temp. °C. | MMA Conversion | Selectivity |
|---|---|---|---|
| 0.353 | 300 | 16 | 100 |
| 0.111 | 250 | 19 | 100 |
| 0.517 | 300 | 25 | 100 |
| 0.346 | 300 | 29 | 100 |
| 0.661 | 375 | 37 | 98 |
| 0.554 | 325 | 39 | 96 |
| 0.651 | 350 | 43 | 95 |
| 0.176 | 300 | 52 | 98 |
| 0.393 | 350 | 58 | 97 |
| 0.661 | 400 | 64 | 95 |
| 0.554 | 350 | 65 | 91 |
| 0.196 | 350 | 65 | 96 |
| 0.238 | 375 | 66 | 94 |
| 0.661 | 450 | 75 | 86 |

SODIUM MORDENITE CATALYST WITH WATER IN THE FEED

| Mol H₂O/ Mol MMA | Flow Rate —g MMA/ g cat/h | Temp. °C. | MMA Conversion | Selectivity |
|---|---|---|---|---|
| 2.56 | 0.403 | 250 | 16 | 95 |
| 2.56 | 0.806 | 421 | 33 | 96 |
| 2.56 | 0.403 | 419 | 46 | 93 |
| 2.46 | 0.144 | 415 | 53 | 98 |
| 2.58 | 0.269 | 418 | 56 | 91 |
| 2.56 | 0.201 | 420 | 67 | 84 |
| 2.56 | 0.403 | 250 | 73 | 84 |
| 2.56 | 0.403 | 300 | 75 | 68 |

TABLE VI

CALCIUM MORDENITE CATALYST WITHOUT WATER IN THE FEED

| Flow Rate g MMA/g cat/h | Temp. °C. | MMA Conversion | Selectivity |
|---|---|---|---|
| 1.55 | 362 | 16 | 95 |
| 1.033 | 391 | 22 | 90 |
| 2.025 | 390 | 22 | 93 |
| 1.55 | 396 | 27 | 91 |
| 1.033 | 362 | 29 | 84 |
| 1.033 | 396 | 34 | 84 |
| 1.033 | 373 | 37 | 88 |
| 0.692 | 369 | 38 | 91 |
| 1.033 | 388 | 59 | 81 |
| 1.033 | 395 | 65 | 77 |
| 0.692 | 404 | 66 | 76 |
| 1.033 | 415 | 73 | 62 |

CALCIUM MORDENITE CATALYST WITH WATER IN THE FEED

| Mol H₂O/ Mol MMA | Flow Rate - g MMA/ g cat/h | Temp. °C. | MMA Conversion | Selectivity |
|---|---|---|---|---|
| 2.58 | 0.252 | 343 | 18 | 100 |
| 2.56 | 0.378 | 368 | 52 | 92 |
| 2.56 | 0.378 | 397 | 53 | 90 |
| 2.56 | 0.378 | 350 | 55 | 92 |
| 2.56 | 0.378 | 403 | 56 | 91 |
| 2.56 | 0.378 | 417 | 59 | 88 |
| 2.56 | 0.378 | 387 | 63 | 88 |
| 2.58 | 0.252 | 367 | 63 | 88 |
| 2.58 | 0.252 | 389 | 66 | 69 |
| 2.58 | 0.252 | 388 | 71 | 79 |

TABLE VII

NATURAL FERRIERITE CATALYST WITHOUT WATER IN THE FEED

| Flow Rate g MMA/g cat/h | Temp. °C. | MMA Conversion | Selectivity |
|---|---|---|---|
| 0.623 | 250 | 17 | 100 |
| 0.623 | 275 | 22 | 100 |
| 0.602 | 300 | 30 | 100 |
| 0.602 | 325 | 47 | 100 |
| 0.567 | 350 | 59 | 98 |
| 0.692 | 385 | 62 | 98 |
| 0.61 | 375 | 65 | 97 |
| 0.256 | 350 | 66 | 95 |
| 0.186 | 350 | 68 | 94 |
| 0.623 | 400 | 71 | 94 |
| 0.706 | 400 | 71 | 96 |
| 0.589 | 425 | 74 | 87 |

NATURAL FERRIERITE CATALYST WITH WATER IN THE FEED

| Mol H₂O/ Mol MMA | Flow Rate —g MMA/ g cat/h | Temp. °C. | MMA Conversion | Selectivity |
|---|---|---|---|---|
| 2.56 | 0.403 | 342 | 39 | 100 |
| 2.56 | 0.403 | 370 | 52 | 100 |
| 2.56 | 0.403 | 356 | 56 | 100 |
| 2.56 | 0.403 | 390 | 59 | 100 |
| 2.56 | 0.403 | 360 | 63 | 100 |
| 2.56 | 0.403 | 410 | 63 | 100 |
| 2.56 | 0.403 | 430 | 64 | 100 |
| 2.56 | 0.403 | 390 | 68 | 97 |
| 2.56 | 0.474 | 400 | 70 | 98 |
| 2.56 | 0.403 | 380 | 72 | 95 |
| 2.56 | 0.403 | 420 | 72 | 97 |
| 2.56 | 0.237 | 397 | 74 | 96 |
| 2.56 | 0.237 | 423 | 75 | 87 |
| 2.56 | 0.403 | 400 | 75 | 91 |
| 2.56 | 0.237 | 416 | 75 | 93 |

TABLE VIII

CALCIUM FERRIERITE CATALYST WITHOUT WATER IN THE FEED

| Flow Rate g MMA/g cat/h | Temp. °C. | MMA Conversion | Selectivity |
|---|---|---|---|
| 1.54 | 325 | 28 | 97 |
| 0.899 | 313 | 32 | 98 |
| 0.909 | 331 | 43 | 96 |
| 0.951 | 349 | 53 | 94 |
| 0.909 | 350 | 54 | 93 |
| 1.137 | 366 | 60 | 91 |
| 0.992 | 376 | 69 | 85 |
| 1.343 | 384 | 69 | 85 |
| 1.033 | 389 | 71 | 82 |

CALCIUM FERRIERITE CATALYST WITH WATER IN THE FEED

| Mol H₂O/ Mol MMA | Flow Rate —g MMA/ g cat/h | Temp. °C. | MMA Conversion | Selectivity |
|---|---|---|---|---|
| 2.56 | 0.806 | 310 | 34 | 100 |
| 2.56 | 0.403 | 309 | 40 | 98 |
| 2.56 | 0.403 | 322 | 52 | 91 |
| 2.56 | 0.403 | 330 | 63 | 84 |
| 2.56 | 0.403 | 351 | 63 | 87 |
| 2.56 | 0.403 | 370 | 72 | 81 |

TABLE IX

NATURAL CLINOPTILOLITE CATALYST WITHOUT WATER IN THE FEED

| Flow Rate g MMA/g cat/h | Temp. °C. | MMA Conversion | Selectivity |
|---|---|---|---|
| 0.346 | 250 | 25 | 98 |
| 0.692 | 250 | 42 | 81 |
| 0.692 | 300 | 52 | 91 |
| 0.346 | 304 | 56 | 90 |
| 0.692 | 347 | 64 | 79 |

NATURAL CLINOPTILOLITE CATALYST WITH WATER IN THE FEED

| Mol H₂O/ Mol MMA | Flow Rate —g MMA/ g cat/h | Temp. °C. | MMA Conversion | Selectivity |
|---|---|---|---|---|

TABLE IX-continued

| | | | | |
|---|---|---|---|---|
| 2.56 | 0.806 | 371 | 57 | 99 |
| 2.56 | 0.605 | 374 | 60 | 98 |
| 2.56 | 0.806 | 353 | 64 | 95 |
| 2.56 | 0.403 | 386 | 69 | 89 |
| 2.56 | 0.403 | 402 | 74 | 85 |
| 2.56 | 0.403 | 374 | 74 | 95 |

TABLE X

NATURAL PHILLIPSITE CATALYST WITHOUT WATER IN THE FEED

| Flow Rate g MMA/g cat/h | Temp. °C. | MMA Conversion | Selectivity |
|---|---|---|---|
| 0.692 | 300 | 15 | 100 |
| 3.038 | 353 | 19 | 97 |
| 3.038 | 371 | 31 | 96 |
| 0.692 | 447 | 35 | 92 |
| 3.038 | 390 | 46 | 94 |
| 3.038 | 405 | 62 | 89 |

NATURAL PHILLIPSITE CATALYST WITH WATER IN THE FEED

| Mol H$_2$O/ Mol MMA | Flow Rate —g MMA/ g cat/h | Temp. °C. | MMA Conversion | Selectivity |
|---|---|---|---|---|
| 2.57 | 0.465 | 340 | 23 | 100 |
| 2.57 | 0.465 | 379 | 42 | 97 |
| 2.57 | 0.62 | 401 | 42 | 98 |
| 2.57 | 0.465 | 359 | 43 | 98 |
| 2.57 | 0.465 | 398 | 53 | 97 |
| 2.57 | 0.465 | 418 | 58 | 97 |
| 2.57 | 0.465 | 402 | 59 | 95 |

EXPERIMENTS 1-4

The following experiments are intended to demonstrate the use of amination catalysts in processes which are outside the invention because the catalysts do not exhibit the selectivities exhibited by the catalyst of the process of the invention, both in the absence of and presence of water in the system. The conditions employed in carrying out the processes were substantially the same as described hereinabove in the examples. Pertinent data regarding Experiments 1-4 are summarized in Table XI-XIV, respectively. Experiments 1 and 2 demonstrate the use of catalysts which are non-selective in either system, that is, one which is dry or one which contains water. Data from Experiment 1, including data not shown in Table XI, are represented graphically in FIG. 1. Experiments 3 and 4 demonstrate the use of catalysts which are selective in a dry system but non-selective in a system which contains water. Data from Experiment 3, including data not shown in Table XIII, are represented graphically in FIG. 2. Experiment 3, as is the comparative experiment, using η-Al$_2$O$_3$, included in Example 3, is representative of the processes of the aforesaid U.S. Pat. No. 1,926,691.

TABLE XI

SILICA-ALUMINA CATALYST WITHOUT WATER IN THE FEED

| Flow Rate g MMA/g cat/h | Temp. °C. | MMA Conversion | Selectivity |
|---|---|---|---|
| 0.658 | 275 | 23 | 79 |
| 0.692 | 300 | 32 | 71 |
| 0.138 | 225 | 33 | 65 |
| 0.187 | 250 | 34 | 64 |
| 0.658 | 300 | 36 | 68 |
| 0.52 | 300 | 39 | 66 |
| 0.346 | 300 | 55 | 57 |
| 0.346 | 300 | 56 | 54 |
| 0.623 | 325 | 58 | 56 |
| 0.589 | 350 | 69 | 50 |

SILICA-ALUMINA CATALYST WITH WATER IN THE FEED

| Mol H$_2$O/ Mol MMA | Flow Rate —g MMA/ g cat/h | Temp. °C. | MMA Conversion | Selectivity |
|---|---|---|---|---|
| 2.56 | 0.403 | 325 | 22 | 78 |
| 2.56 | 0.403 | 345 | 36 | 66 |
| 2.56 | 0.403 | 364 | 47 | 63 |
| 2.56 | 0.403 | 380 | 56 | 59 |

TABLE XII

SODIUM OFFRETITE CATALYST WITHOUT WATER IN THE FEED

| Flow Rate g MMA/g cat/h | Temp. °C. | MMA Conversion | Selectivity |
|---|---|---|---|
| 0.692 | 265 | 51 | 58 |

SODIUM OFFRETITE CATALYST WITH WATER IN THE FEED

| Mol H$_2$O/ Mol MMA | Flow Rate —g MMA/ g cat/h | Temp. °C. | MMA Conversion | Selectivity |
|---|---|---|---|---|
| 2.56 | 1.209 | 263 | 24 | 89 |
| 2.56 | 1.209 | 292 | 46 | 62 |
| 2.56 | 1.209 | 321 | 68 | 49 |

TABLE XIII

γ-ALUMINA CATALYST WITHOUT WATER IN THE FEED

| Flow Rate g MMA/g cat/h | Temp. °C. | MMA Conversion | Selectivity |
|---|---|---|---|
| 0.692 | 300 | 26 | 98 |
| 0.484 | 375 | 35 | 98 |
| 0.692 | 345 | 43 | 100 |
| 0.692 | 378 | 48 | 94 |
| 0.503 | 370 | 59 | 92 |
| 0.503 | 384 | 66 | 87 |
| 0.588 | 391 | 66 | 98 |
| 0.838 | 421 | 72 | 78 |
| 0.692 | 372 | 74 | 94 |
| 0.503 | 385 | 75 | 74 |
| 1.003 | 403 | 75 | 81 |

γ-ALUMINA CATALYST WITH WATER IN THE FEED

| Mol H$_2$O/ Mol MMA | Flow Rate —g MMA/ g cat/h | Temp. °C. | MMA Conversion | Selectivity |
|---|---|---|---|---|
| 5.15 | 0.207 | 378 | 15 | 95 |
| 5.15 | 0.207 | 409 | 28 | 83 |
| 5.25 | 0.103 | 373 | 32 | 83 |
| 2.56 | 0.403 | 380 | 32 | 84 |
| 2.56 | 0.403 | 390 | 38 | 74 |
| 5.25 | 0.103 | 389 | 44 | 73 |
| 2.56 | 0.403 | 400 | 50 | 69 |
| 5.25 | 0.103 | 400 | 56 | 64 |
| 5.25 | 0.103 | 401 | 58 | 66 |
| 2.56 | 0.403 | 411 | 60 | 61 |
| 5.25 | 0.103 | 409 | 60 | 67 |
| 5.25 | 0.103 | 427 | 68 | 62 |
| 5.25 | 0.103 | 426 | 69 | 61 |
| 2.56 | 0.403 | 420 | 70 | 55 |

TABLE XIV

NATURAL ERIONITE CATALYST WITHOUT WATER IN THE FEED

| Flow Rate g MMA/g cat/h | Temp. °C. | MMA Conversion | Selectivity |
|---|---|---|---|
| 1.292 | 296 | 21 | 98 |
| 1.736 | 332 | 42 | 96 |

TABLE XIV-continued

| | | | |
|---|---|---|---|
| 1.261 | 316 | 43 | 98 |
| 1.302 | 361 | 66 | 89 |
| 1.23 | 353 | 73 | 93 |
| 1.571 | 380 | 75 | 85 |

NATURAL ERIONITE CATALYST WITH WATER IN THE FEED

| Mol $H_2O$/ Mol MMA | Flow Rate —g MMA/ g cat/h | Temp. °C. | MMA Conversion | Selectivity |
|---|---|---|---|---|
| 2.56 | 0.756 | 343 | 36 | 88 |
| 2.56 | 0.756 | 380 | 40 | 93 |
| 2.46 | 1.259 | 338 | 50 | 81 |
| 2.56 | 0.756 | 362 | 58 | 78 |
| 2.56 | 0.756 | 384 | 69 | 69 |

I claim:

1. Improved continuous process for disproportionating monomethylamine to dimethylamine and ammonia, said process comprising passing monomethylamine over the crystalline aluminosilicate catalyst selected from (a) mordenite wherein the primary cation is Na, HNa having at least 2% Na by weight, Mg, Ca, Sr or Ba (b) ferrierite wherein the primary metal cation is Na, K, Mg, Ca, Sr or Ba (c) clinoptilolite and (d) phillipsite, at a temperature of 250°–475° C. and a pressure of 7–7000 KPa, at a feed rate of 0.1–10 g of monomethylamine/g of catalyst per hour, at a monomethylamine conversion of 15–75%.

2. Process of claim 1 wherein the temperature is 350°–400° C., the pressure is 70–3000 kPa and the feed rate is 0.5–2 g of monomethylamine/g of catalyst per hour.

3. Process of claim 1 wherein the monomethylamine is anhydrous.

4. Process of claim 1 wherein the monomethylamine is admixed with water.

5. Process of claim 1 wherein the catalyst is sodium mordenite.

6. Process of claim 1 wherein the catalyst is hydrogen-sodium mordenite having at least 2% Na by weight.

7. Process of claim 1 wherein the catalyst is calcium mordenite.

8. Process of claim 1 wherein the catalyst is natural ferrierite.

9. Process of claim 1 wherein the catalyst is natural ferrierite which has been subjected to calcium ion exchange.

* * * * *